United States Patent [19]
Todd et al.

[11] Patent Number: 5,437,651
[45] Date of Patent: Aug. 1, 1995

[54] MEDICAL SUCTION APPARATUS

[75] Inventors: Robert J. Todd; Jaime E. Yagge, both of Salt Lake City, Utah; James E. Lowe, Durham, N.C.; Terry M. Wonder, Salt Lake City, Utah

[73] Assignee: Research Medical, Inc., Salt Lake City, Utah

[21] Appl. No.: 116,201

[22] Filed: Sep. 1, 1993

[51] Int. Cl.⁶ .............................................. A61M 1/00
[52] U.S. Cl. ................................ 604/313; 604/317; 604/323; 604/902; 15/420
[58] Field of Search ................ 128/846, 847, 849–852; 604/19, 27–28, 30, 32–35, 289–290, 312–314, 317, 322–323, 326, 902

[56] References Cited

U.S. PATENT DOCUMENTS

| | | | |
|---|---|---|---|
| 2,027,543 | 1/1936 | Lofgren | 15/420 |
| 2,305,289 | 12/1942 | Loburg | 128/850 |
| 2,528,278 | 10/1950 | Kendrick | 15/420 |
| 2,966,694 | 1/1961 | Brown, Jr. | 15/420 |
| 3,520,300 | 7/1970 | Flower, Jr. | 604/902 |
| 4,193,156 | 3/1980 | Chauvier | 15/420 |
| 4,533,352 | 8/1985 | Van Beek et al. | 604/313 |
| 5,014,389 | 5/1991 | Ogilvie et al. | 15/415.1 |
| 5,034,006 | 7/1991 | Hosoda et al. | 604/317 |

OTHER PUBLICATIONS

Biological Thresholds of Cold-Induced Phrenic Nerve Injury, The Journal of Thoracic and Cardiovascular Surgery, Francis Robicsek, M.D. et al, 1990, 9:167–170.
The Effect of Pericardial Insulation on Hypothermic Phrenic Nerve Injury During Open-Heart Surgery, The Annals of Throacic Surgery, Rick A. Esposita, M.D. et al, vol. 43, No. 3, Mar. 1987.
Elevated Hemidiaphragm After Cardiac Operations: Incidence, Prognosis, and Relationship to the Use of Topical Ice Slush, The Annals of Thoracic Surgery, Jack J. Curtis, M.D. et al, 48:764–768, 1989.
Phrenic Nerve Paresis Associated with the Use of Iced Slush and the Cooling Jacket for Topical Hypothermia, The Journal of Throacic and Cardiovascular Surgery, John A. Rousou, M.D. et al, 1985, 89:921–925.

Primary Examiner—Randall L. Green
Assistant Examiner—P. Zuttarelli
Attorney, Agent, or Firm—Workman, Nydegger & Seeley

[57] ABSTRACT

The present invention is directed to a new and useful apparatus and method for absorbing and collecting blood and other fluids which accumulate in a patient during surgical procedures. An absorbent portion is connected to a suction source. When the absorbent portion is placed in contact with the fluid to be collected, the fluid is absorbed by the absorbent portion. Operation of the suction source provides a vacuum which draws the fluid away from the absorbent portion and out of the body. The fluid can be drawn into a receptacle for later cleansing and reuse. A flexible backing plate is attached to the absorbent portion. Channels formed a long the backing plate direct the vacuum evenly across the absorbent portion of the device such that fluid is drawn evenly from the absorbent portion. Suction tubing connects the absorbent portion to the suction source. The absorbent portion and attached backing plate can be folded to fit into small areas.

33 Claims, 7 Drawing Sheets

MEDICAL SUCTION APPARATUS

BACKGROUND

1. Field of the Invention

The present invention relates to methods and apparatus for collecting blood and other interstitial fluids which are lost from a patient during a surgical procedure. More particularly, the present invention relates to the use of suction for collecting the blood and other fluids for later reuse.

1. Background of the Art

During surgical procedures, blood, saline solutions, and other liquid substances collect within and around incision sites. Accumulation of these fluids can obstruct the vision of the surgeon or other medical personnel performing the procedure. Therefore, it is desired that these fluids be quickly and efficiently cleared away from the area upon which the surgery is taking place.

At present, it is a universal practice to utilize gauze pads to absorb the fluids. In a typical thoracic procedure, it is common to use literally hundreds of gauze pads. These pads are placed into the area of excess fluid and the fluid is absorbed. Once the gauze pads are soaked, they are removed from the patient's body and replaced with new pads. continuous replacement of the gauze pads leads to use of very large numbers of pads.

Once saturated, the pads often blend into the internal environment of the body. Unfortunately, this can make it very difficult for the gauze pads to be seen and distinguished from the blood, fluids and body parts. Because of this, it occasionally occurs that gauze pads are accidentally left inside the body after the surgical procedure is completed.

Typically, the number of gauze pads retrieved from the body is carefully counted after the procedure and compared with the number actually used. If there is a discrepancy between the two numbers, the physician may be required to reopen the patient in order to find any pads which were overlooked during the course of the surgery. This multiplies the patient's discomfort and chances for infection.

Another problem with the use of gauze pads for the absorption of blood from a patient's body is that it results in disposal of blood which could otherwise be collected and reused. It is often desired to collect blood lost from a patient during a surgical procedure. This collected blood can be cleansed for reintroduction into the patient's body. Through this collection process, the patient can be given his or her own blood to replace the blood lost. The need for blood transfusions from other sources is reduced, thereby reducing the risk of infection passed in third party blood or other detrimental effects due to introduction of blood from another person.

Unfortunately, blood cannot be collected through the use of gauze pads. Once the gauze pads are saturated with the blood, they are removed, counted, and discarded. The absorbed blood is discarded along with the pads. Great quantities of blood are wasted. Great quantities of gauze pads are also wasted.

An additional problem with the use of gauze pads is the difficulty of placing the pads in small areas, such as between tissues or beneath the heart, in order to absorb blood and other fluids from those areas. Such gauze pads are quickly saturated, requiring frequent replacement. Further, once saturated, it can be difficult to locate the gauze pads within such areas.

Some attempts have been made to replace the use of gauze pads with other apparatus or procedures. For example, several collection reservoir tray structures have been devised which are placed under a body organ or under the body area involved in surgery so as to collect body fluids draining from the surgical site. There are serious limitations to the uses of such devices, however, such as an inability to collect all body fluids which tend to pool in areas surrounding an incision or in situations where the surgery does not involve an organ or body area which is movable so as to place a tray there beneath.

A common method of dealing with some of these other problem areas is the use of a suction wand, typically fitted with a sponge tip to prevent injury to the tissue against which it is placed. The use of a suction wand suffers from the problem that it requires an operator to direct it, and it is not effective for continuous drainage of large areas. Accordingly, even though suction wands are commonly used, it is nevertheless necessary to use large numbers of gauze pads to soak up fluids in most surgical procedures.

BRIEF SUMMARY AND OBJECTS OF THE INVENTION

It is a primary object of the present invention to provide an apparatus and method for quickly and efficiently absorbing and collecting blood and other fluids which accumulate in a patient during surgical procedures.

Another object of the present invention is to provide an apparatus and method for absorbing and collecting blood from a patient during surgical procedures in a manner such that the blood can be later reintroduced into the patient.

A further object of the present invention is to provide an apparatus and method for absorbing and collecting blood and other fluids from a patient during surgical procedures in a manner which reduces the number of gauze pads used during the surgical procedure.

Yet another object of the present invention is to provide an apparatus and method for absorbing and collecting blood from a patient during surgical procedures in a manner which reduces the risk of losing gauze pads within the patient's body.

A further object of the present invention is to provide an apparatus and method for efficiently absorbing and collecting blood during cardiac surgery.

Additional objects and advantages of the invention are set forth herein below in the detailed description, or will be appreciated by the practice of the invention.

To achieve the foregoing objects, and in accordance with the invention as embodied and broadly described herein, the present invention is directed to a new and useful apparatus for use in absorbing and collecting blood and other interstitial fluids which accumulate at incision sites during surgical procedures. The blood, once collected, can be cleansed and reintroduced into the patient, thus saving the patient from the need of blood transfusions using blood from others.

The presently preferred embodiment of the present invention includes an absorbing means which is to be placed in the area where fluid is to be collected and in communication with that fluid. The absorbing portion is sized so as to be able to absorb fluid from a relatively broad surface area.

Attached to the absorbing means is a thin backing plate which is preferably flexible and capable of being bent into various positions. An orifice is advantageously formed into the backing plate, generally in a central location. Attached to this orifice is a suction tube which can connect the backing plate to a suction source. When the suction source is operated, a suction force is applied through the suction tube to the backing plate and to the connected absorbing portion.

Also formed into the backing plate is a plurality of protrusions extending from the backing plate into the absorbing portion. The plurality of protrusions form channels which are wider at locations farther from the central orifice and more narrow at locations closer to the central orifice. When the suction force is applied, this arrangement of the plurality of protrusions works to evenly distribute the suction force along the area of the absorbing portion. This allows more uniform collection of fluids from the absorbing portion.

The shape of the backing plate can be determined by what shape and size will fit best in the area into which the backing plate will be inserted. For example, an egg-shaped backing plate may be the best shape for positioning beneath the heart during cardiac surgery.

BRIEF DESCRIPTION OF THE DRAWINGS

In order to more fully understand the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention in its presently understood best mode for making and using the same will be described with additional specificity and detail through the use of the accompanying drawings in which.

DETAILED DESCRIPTION OF THE PREFERRED EMBODIMENTS

A. Apparatus for Absorbing and Collecting Blood and Other Fluids

The present invention is directed to a method and apparatus for use in surgical procedures for absorbing and collecting blood and other fluids which accumulate around the surgical sites. More particularly, the present invention is directed to the use of suction to clear away the blood and fluid and to collect the blood for later reintroduction into the patient.

Figure 1:
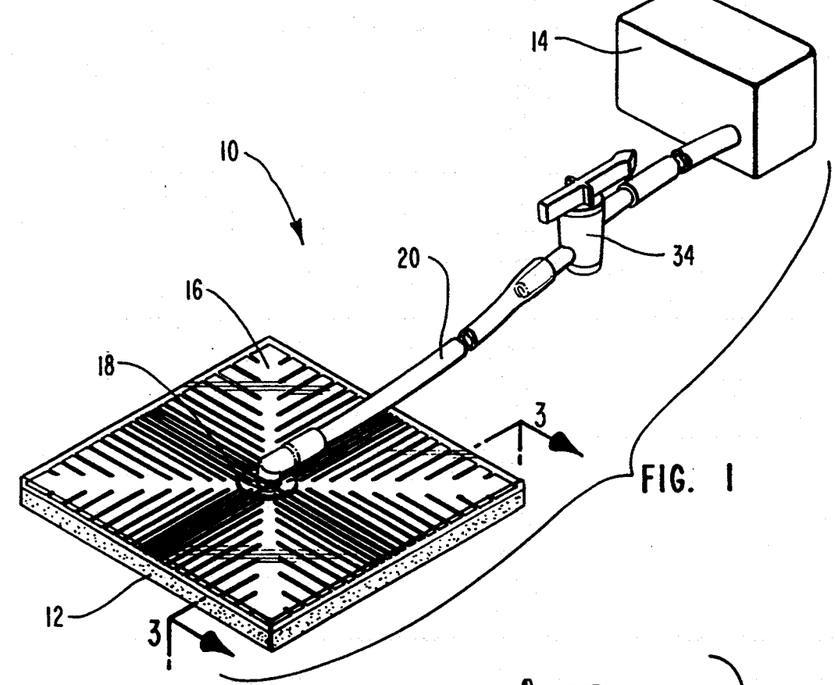
FIG. 1 is a perspective view illustrating a presently preferred embodiment of the apparatus of the present invention.

Referring to the drawings, FIG. 1 depicts one presently preferred embodiment of an apparatus, generally labelled 10, for absorbing and collecting blood.

During a surgical procedure, excess blood and other interstitial fluids often collect around the incision sites. These fluids, if not removed, can obstruct the vision of the surgeon and other medical personnel. Apparatus 10 of the present invention is used to absorb the excess fluids and remove them from the body.

The absorbing portion of apparatus 10 comprises absorbing means for contacting and absorbing the fluid to be collected. The absorbing means is shaped to conform to the area where fluid is to be collected. When the absorbing means contacts the fluid, the fluid is absorbed and the surgical area is kept clean and free from excess blood and fluids. The absorbing means is constructed of a porous material through which intake of fluids readily occurs.

In one embodiment of the present invention which is illustrated in FIG. 1, the absorbing means is a polyurethane open celled foam pad 12. The preferred foam pad has a 100 $\mu$ pore size. All sizes capable of absorbing fluid, however, are within the scope of the present invention. Foam pad 12 is attachable to a suction source 14 for providing suction such that the fluid absorbed into foam pad 12 is drawn away. Suction source 14 may be any mechanism which can provide an appropriate suction vacuum. A receptacle may be attached to the apparatus to collect the fluid as it is drawn from the body.

Attached to foam pad 12 is backing means for supporting the absorbing means. As seen in the embodiment illustrated in FIG. 1 and in the exploded view of FIG. 2, the backing means comprises a flexible backing plate 16 which is attached to one surface of foam pad 12 so as to provide support. The cross-sectional view of FIG. 3 illustrates the attachment of backing plate 16 to foam pad 12.

Backing plate 16 is preferably constructed of a flexible and pliable material which can be bent and manipulated. This allows foam pad 12, attached to flexible backing plate 16, to be folded into various configurations to fit into various areas of the body with the absorbent portion facing outward. The folded foam pad 12 can be positioned in small places where a large apparatus could not otherwise fit, and in places such as between tissues wherein absorbency on two sides is desired. In the preferred embodiment, the material of backing plate 16 is a polyvinylchloride plastisol. However, other flexible, pliant materials which are benign to tissue can also be used within the scope of the present invention.

Figure 6:
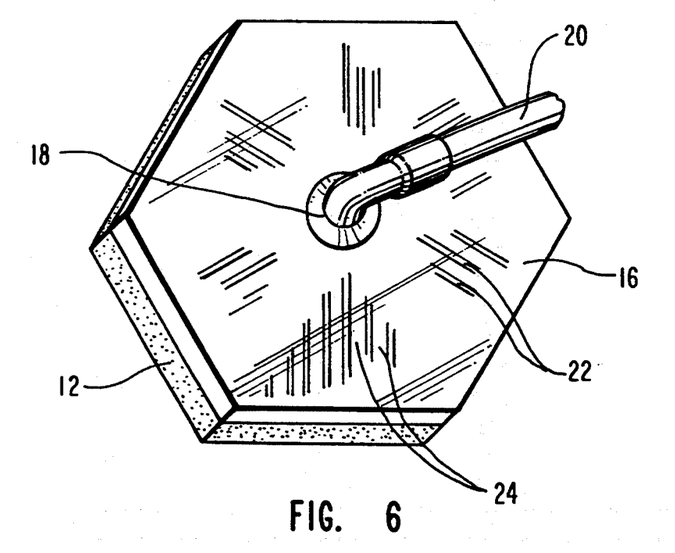
FIG. 6 is a perspective view of an alternate embodiment of the backing plate of the apparatus of the present invention wherein the backing plate is in a hexagonal shape.
Figure 7:
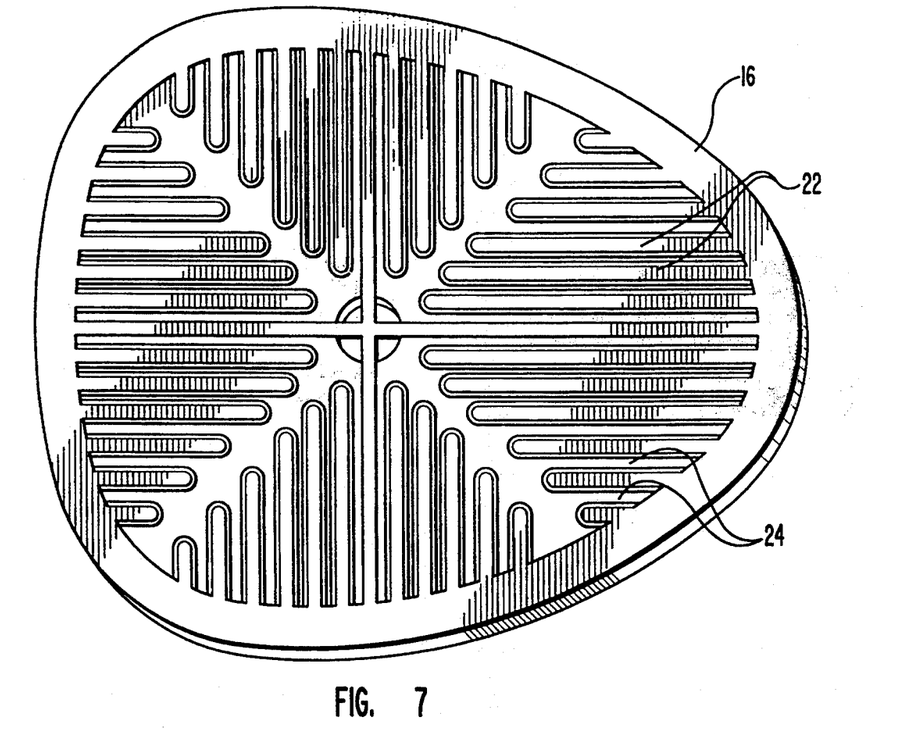
FIG. 7 is a perspective view illustrating a backing plate of the present invention which is egg-shaped.

The shape of backing plate 16 may vary, in order to conform to specific areas from which fluid is to be collected, and to allow for the greatest amount and most uniform method of absorption and collection. For example, FIG. 6 illustrates the backing plate 16 formed into a hexagonal shape. FIG. 7 illustrates an egg-shaped backing plate. The egg shape is a modified oval shape wherein one end is wider than the other. This shape is preferable for placement under the heart during cardiac surgery. The preferred embodiment of the egg shaped plate has a length of about 3.5 inches and a width of about 3.0 inches.

Figure 8:
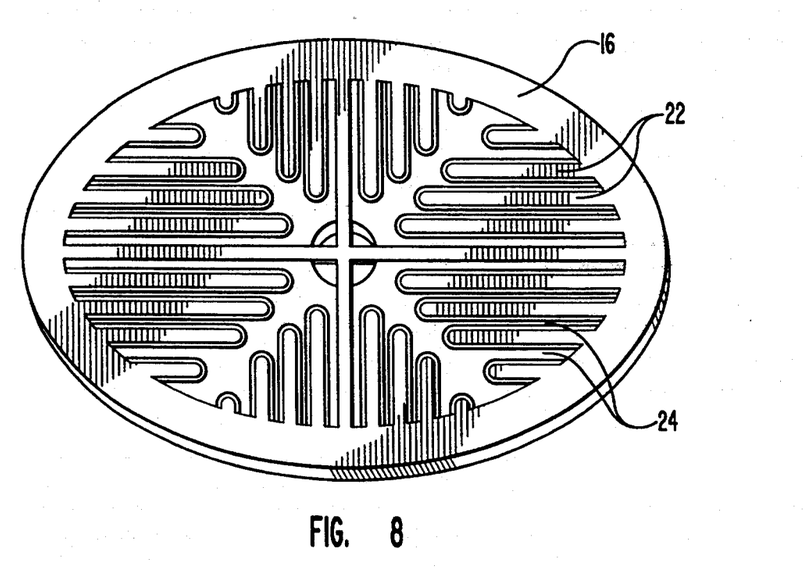
FIG. 8 is a perspective view illustrating a backing plate of the present invention which has an elliptical shape.
Figure 9:
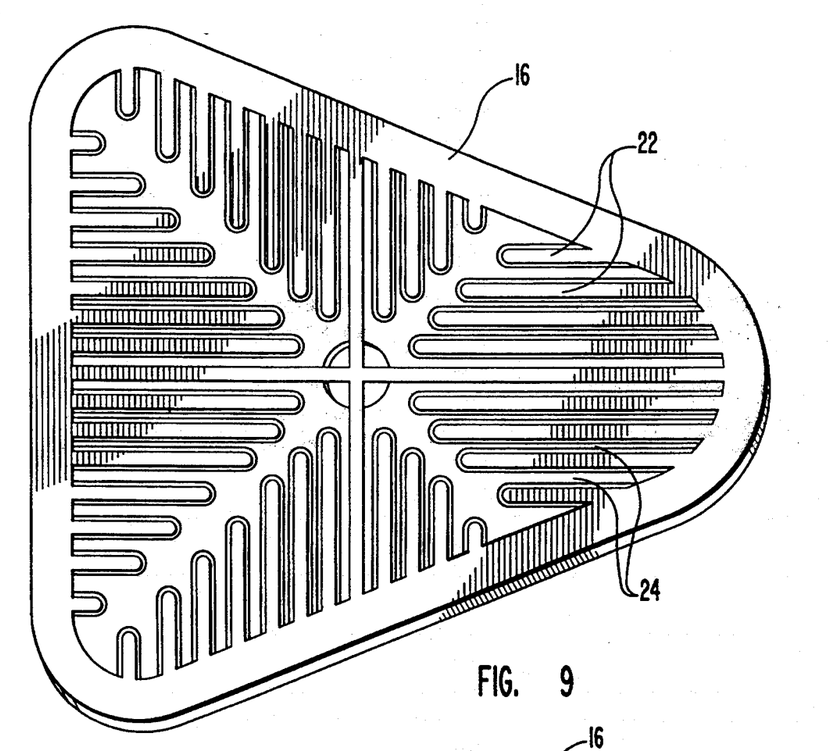
FIG. 9 is a perspective view illustrating a backing plate of the present invention which has a triangular shape.
Figure 10:
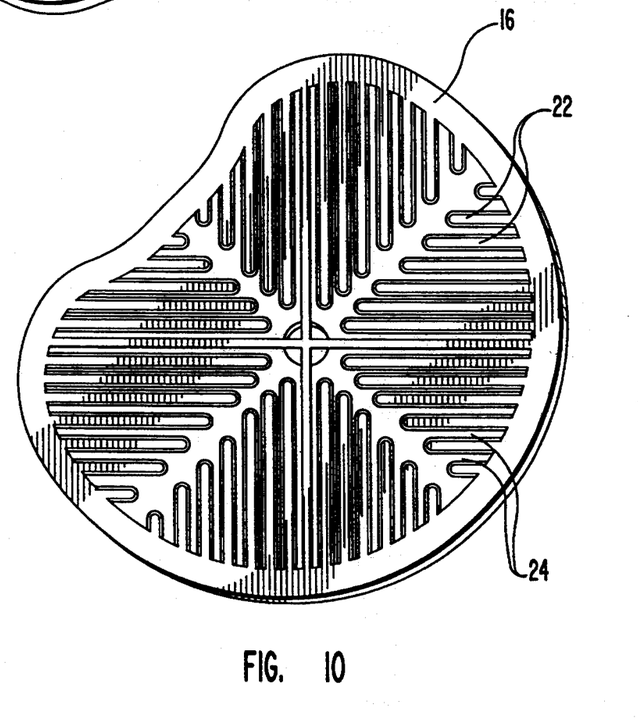
FIG. 10 is a perspective view illustrating a backing plate of the present invention which has a round shape which is slightly concave.
Figure 11:
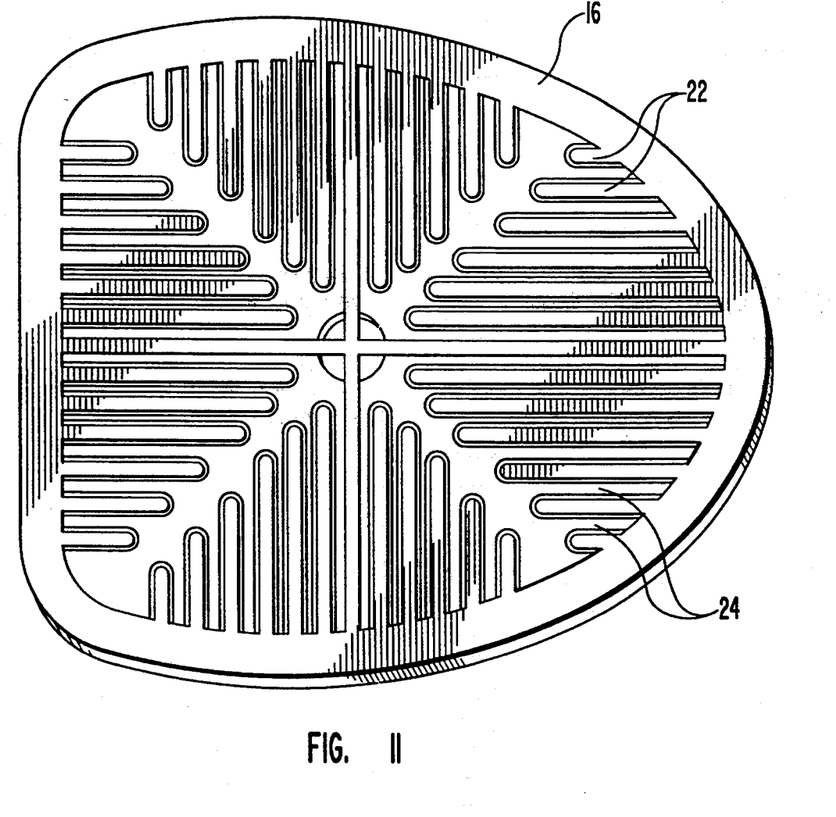
FIG. 11 is a perspective view illustrating a backing plate of the present invention which has an elliptical shape truncated on one side.
Figure 12:
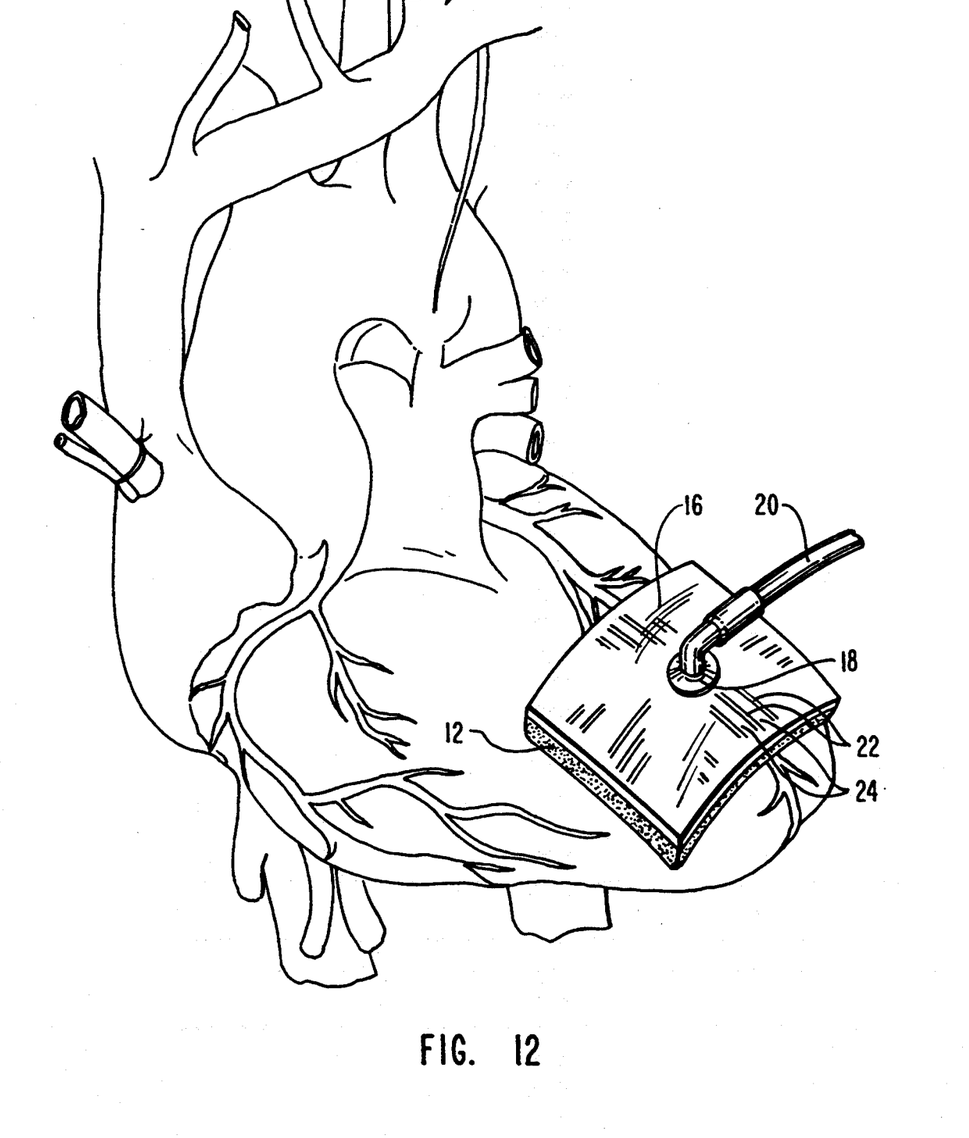
FIG. 12 is a perspective view of the invention illustrating the apparatus over a patient's organ.

Other examples of possible shapes are illustrated in FIGS. 8–11. FIG. 8 illustrates an elliptical shape. It is preferred that the elliptical shape have a length of about 3.0 inches and a width of about 2.0 inches. FIG. 9 illustrates a triangular shape wherein the corners of the triangle are rounded. Again, a length of about 3 inches of a FIG. 9 3.0 inches and a width of about 2.0 inches. FIG. 9 illustrates a triangular shape wherein the corners of the triangle are rounded. Again, a length of about 3 inches of a width at the base of about 2 inches is preferred. FIG. 10 illustrates a round shape which is slightly concave on one side. FIG. 11 illustrates an elliptical shape which is truncated on one side.

The backing plate 16, with attached foam pad 12, may also be formed into various different sizes. At present, three preferred sizes for the square shape are 6 inches by 6 inches, 4 inches by 4 inches, and 2 inches by 2 inches. Other convenient sizes are possible and can be chosen with respect to ease of insertion of placement in the particular surgical areas involved.

Figure 2:
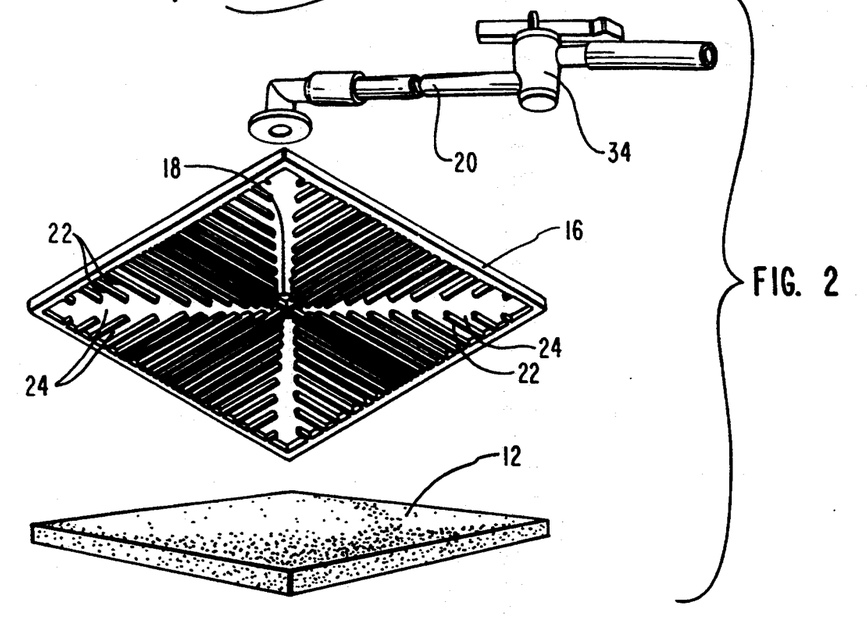
FIG. 2 is an exploded view of the apparatus of FIG. 1.
Figure 3:
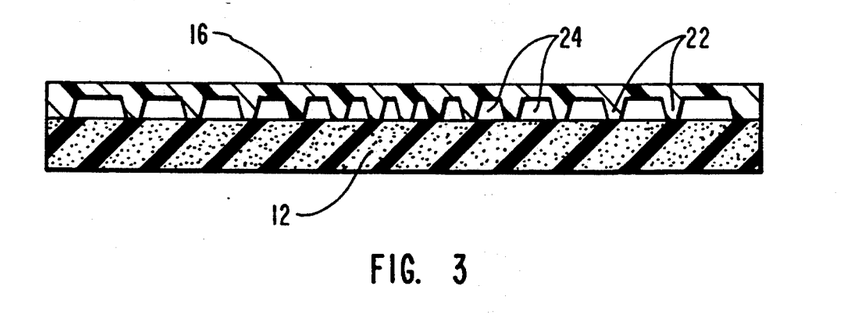
FIG. 3 is a cross-sectional view of the absorbing portion and the backing plate, taken along lines 3—3 of FIG. 1.

As can be seen in FIGS. 1–3, an orifice 18 is formed into backing plate 16 in a substantially central position. It is through orifice 18 that the vacuum from suction source 14 is applied to foam pad 12. Delivery means for connecting the backing plate 16 to suction source 14, such that suction can be applied to the absorbing means, are attached to orifice 18. As can be seen in FIGS. 1 and 2, delivery means of the preferred embodiment comprises a length of tubing 20 stretching from suction source 14 to backing plate 16, and When suction source 14 is operated, the vacuum is directed through tubing 20 in such way that fluid which has been absorbed into foam pad 12 is drawn away from foam pad 12, through backing plate 16, and through tubing 20 towards suction source 14. When the fluid reaches suction source 14, it is collected into a fluid receptacle (not shown) where it is available for cleaning and reuse, if desired.

An important aspect of backing plate 16 comprises flow control means for distributing the vacuum from suction source 14 substantially evenly across the surface of foam pad 12 so as to allow substantially even suction of the absorbed fluid from foam pad 12. The flow control means assists in preventing situations wherein some portions of foam pad 12 are affected strongly by the vacuum and remain dry while other portions become and remain saturated.

Figure 4:
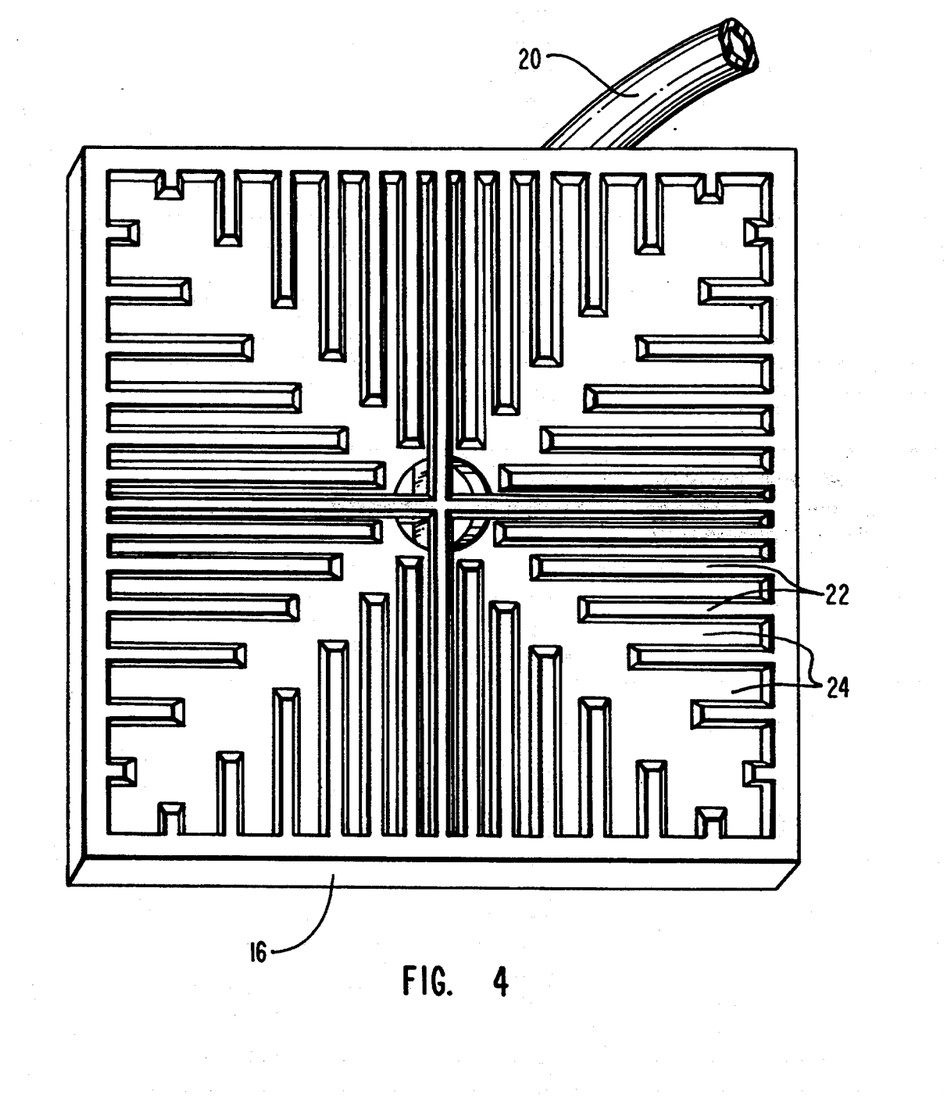
FIG. 4 is a perspective view illustrating the backing plate of the apparatus of FIG. 1.

FIG. 4 illustrates the presently preferred embodiment of the flow control means within the scope of the present invention. Backing plate 16 is shown in a square shape. Again, while backing plate 16 may be formed into many different shapes depending upon the area in which fluid is to be collected, the square shape will be used as the example for explaining the various other features of the present invention. As seen in FIG. 4, the flow control means comprises a plurality of ridges 22 protruding from backing plate 16 towards the attached foam pad 12. The plurality of ridges 22 is positioned on backing plate 16 such that a channel 24 is formed between each adjacent pair of ridges 22 in a direction extending away from the orifice of the backing plate.

In the square shaped backing plate 16 of FIG. 4, ridges 22 are formed such that they are aligned substantially perpendicularly from each side of backing plate 16 toward central orifice 18. Channels 24 are formed between ridges 22 and channels 24 also extend from each of the four corners of backing plate 16 toward central orifice 18. The suction force is distributed to the foam pad 12 through channels 24.

Ridges 22 are formed such that they are positioned closer together towards the center of backing plate 16, and farther apart towards the periphery of backing plate 16. With this arrangement, the channels 24 are narrower at locations closer to central orifice 18 and wider at locations further from central orifice 18. This permits greater flow of material in the wider channels further away from central orifice 18 wherein the force of the vacuum is the weakest, and lesser flow of material in the narrower channels closer to the central orifice 18 wherein the force of the vacuum is the strongest. Such a flow pattern allows the suction of fluid from foam pad 12 to occur more uniformly throughout foam pad 12. It can be appreciated that when designing the size of the channels, the channels should be sized wide enough to allow smooth flow of material, but narrow enough so that the fluid is kept in motion and dead spots do not arise.

Figure 5:
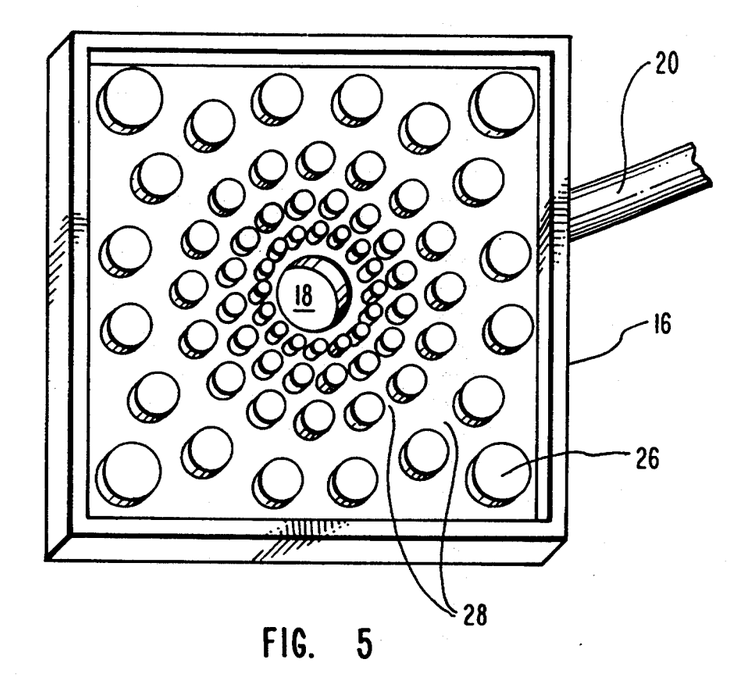
FIG. 5 is a perspective view of an alternate embodiment of the backing plate of the apparatus of the present invention.

Other forms of flow control means may also be utilized to promote even flow of vacuum and even collection of fluid from foam pad 12. FIG. 5 illustrates an alternate embodiment of the flow control means. Rather than a plurality ridges 22, the flow control means may comprise a plurality of posts 26 extending from backing plate 16. Again, channels 28 are formed between the plurality of posts 26 through which the vacuum from suction source 14 is distributed to foam pad 12, and through which the absorbed fluid passes as the fluid is drawn from foam pad 12.

In the presently preferred embodiment within the scope of the present invention, the plurality of posts 26 is positioned around the central orifice 18 in circular formations. Small posts are positioned close together around the central orifice. Moving towards the periphery of backing plate 16, the posts become increasingly larger and are positioned further apart such that the channels formed at locations further away from the central orifice 18 are wider than the channels formed at locations closer to central orifice 18. Again, posts 26 must be positioned such that the channels are wide enough to allow smooth flow of fluid, but narrow enough to avoid dead spots.

It should be noted that other forms of flow control means, which provide for the even distribution of vacuum to the foam pad so that there is even suction of fluid from the foam pad, are available and within the scope of the present invention. For larger embodiments, there may be provided more than one orifice formed into the backing pad so that there can be more than one direct area of suction. Thus, uniform distribution of suction can be more easily accomplished.

Also within the scope of the present invention, the suction can be provided to the absorbing apparatus in either a continuous or an intermittent fashion. With continuous suction, blood and other fluids are continuously and actively drawn into foam pad 12 and into suction tubing 20. With intermittent suction, the blood can be collected from the foam pad 12 as needed. For example, it is preferred that the suction be applied only after foam pad 12 has become soaked with absorbed blood and other fluids. This decreases the air flow into the body, and causes less blood clotting and less hemolysis to the cells to be collected.

Means for permitting intermittent supply of suction such that suction can be applied and discontinued as desired are provided by the present invention. As illustrated in the presently preferred embodiment of FIG. 1, a valve 34, which can be opened and closed as desired, is attached to tubing 20. The user of the apparatus can wait until the foam pad has absorbed as much of the accumulated blood and fluid as it can hold before allowing the suction to operate. Once the foam pad is saturated, the user can open the valve and allow the suction force to be applied. When the foam pad is again dry, the valve can be closed so that suction is stopped. By this method of operation, the blood cells in the fluid to be collected will be subjected to less air flow, and thus less hemolysis and blood clotting will occur.

Other means for providing intermittent supply of suction are also within the scope of the present invention. For example, in an alternate embodiment, a pump could be connected to the apparatus and operated manually or automatically for periodic drainage.

To use the apparatus of the present invention, the first step includes placing the absorbing apparatus against the area from which the fluid is to be collected and connecting the absorbing apparatus to a suction source. Fluid is allowed to be absorbed into the absorbing means. The next step includes operating the suction source such that a vacuum is provided through the delivery means of the apparatus to the absorbing means. The flow control means then works to evenly disperse the suction force along the absorbing means such that fluid is evenly drawn from the absorbing means into the delivery means. The last step includes collecting the fluid drawn from the absorbing means into a fluid receptacle for possible later reuse of the collected fluid. FIG. 7 illustrates the apparatus in possible use during heart surgery. It is preferred that an egg-shaped backing plate and absorbing means be used during cardiac surgery for ease of insertion and placement beneath the heart.

During this method, the suction can be applied constantly or intermittently. As the fluid is drawn away from the absorbing means, the absorbing means will dry and can then absorb more fluid. Continuous replacement of absorbing material is unnecessary.

It should be noted that although the preferred embodiment is that which has been described in detail above, other embodiments of the apparatus for absorbing and collecting blood and other fluids for surgical sites are also within the scope of the invention. For example, the absorbing means may be folded into a serpentine configuration. Further, the absorbing means may be coiled into a coiled tube configuration. Other alternate configurations may also be within the scope of the present invention.

B. Summary

The present invention provides for an apparatus and method for absorbing and collecting blood which has accumulated around incision sites during surgical procedures. Suction is used to draw the fluid out of the body in an a-traumatic manner. The suction is distributed substantially evenly through the absorbent portion of the apparatus such that fluid is evenly drawn out of the body through the absorbent portion and collected. The fluid can be collected in a receptacle for later cleansing and possible reuse.

The apparatus of the present invention can be used continuously during the surgical procedure without the need for replacement. Because of this a smaller number of gauze pads must be used. Consequently, the risk of losing gauze pads within the body of a patient is reduced. Further, the apparatus of the present invention can be folded and sized to be tailored for various areas of the body as desired.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. An apparatus for absorbing and collecting, into a fluid receptacle, blood and other interstitial fluids from a patient during the course of a surgical procedure comprising:
   a. absorbing means for contacting and absorbing the fluid to be collected;
   b. backing means, attached to said absorbing means, for supporting said absorbing means, said backing means having a substantially centrally positioned orifice formed therein;
   c. delivery means, attached to the orifice of the backing means, for receiving suction force a suction source and delivering the suction force to the absorbing means; and
   d. suction force proportioning means, in communication with said backing means and said absorbing means, for directing distribution of the suction force from said suction means such that absorbed fluid is efficiently extracted from the absorbing means.

2. An apparatus as recited in claim 1, wherein the absorbing means comprises a foam pad on which the blood and the fluid collects and is absorbed.

3. An apparatus as recited in claim 2, wherein the absorbing means is comprised of a polyurethane open cell foam pad.

4. An apparatus as recited in claim 1, wherein the backing means attached to said absorbing means comprises a flexible backing plate made of a flexible, pliable material.

5. An apparatus as recited in claim 4, wherein the suction force proportioning means comprises a plurality of ridges protruding from the backing plate towards the attached absorbing means such that channels are formed on the backing plate between the plurality of ridges, the channels extending away from the orifice of the backing plate, and the channels being wider at locations further away from the orifice of the backing plate and more narrow at locations closer to the orifice of the backing plate, thereby distributing the suction force to permit efficient extraction of absorbed fluid from the absorbing means.

6. An apparatus as recited in claim 4, wherein the suction force proportioning means comprises a plurality of posts protruding from the backing plate towards the attached absorbing means, wherein channels are formed between the plurality of posts, the channels extending away from the orifice of the backing plate, and the channels being wider at locations further away from the orifice of the backing plate and more narrow at locations closer to the orifice of the backing plate, thereby distributing the suction force to permit efficient extraction of absorbed fluid from the absorbing means.

7. An apparatus as recited in claim 4, wherein the flexible backing plate comprises a square shape.

8. An apparatus as recited in claim 4, wherein the flexible backing plate comprises a truncated elliptical shape.

9. An apparatus as recited in claim 4, wherein the flexible backing plate comprises a hexagonal shape.

10. An apparatus as recited in claim 4, wherein the flexible backing plate comprises an egg shape.

11. An apparatus as recited in claim 4, wherein the flexible backing plate comprises an elliptical shape.

12. An apparatus as recited in claim 4, wherein the flexible backing plate comprises a round shape which is slightly concave on one side.

13. An apparatus as recited in claim 4, wherein the flexible backing plate comprises a triangular shape wherein the corners are rounded.

14. An apparatus as recited in claim 4, wherein the flexible backing plate comprises a polyvinylchloride plastisol.

15. An apparatus as recited in claim 1, further comprising means for permitting intermittent supply of suction such that suction can be applied and discontinued as desired.

16. An apparatus as recited in claim 15, wherein the means for permitting intermittent supply of suction is a manually operated value.

17. An apparatus as recited in claim 1, wherein the backing means comprises a multiple of orifices formed therein, said multiple of orifices positioned within the backing means and attached to the delivery means so as to provide a multiple of areas to which suction can be directly delivered to the absorbing means.

18. A suction system for absorbing and collecting blood and other interstitial fluids from a patient during surgical procedures into a fluid receptacle for possible reuse comprising:
　a. absorbing means contacting and absorbing fluid to be collected;
　b. a suction source for providing suction through the absorbing means such that the absorbed fluid is drawn away from said absorbing means;
　c. a backing plate, attached to said absorbing means, for supporting said absorbing means, said backing plate having a centrally positioned orifice formed therein; p1 d. delivery means, attached to the orifice of the backing plate, for receiving suction force from the suction source and delivering the suction force to the absorbing means;
　e. suction force proportioning means, in communication with said backing plate and said absorbing means, for distributing the suction force from said suction means such that absorbed fluid is efficiently extracted from the absorbing means.

19. A suction system as recited in claim 18, wherein the absorbing means comprises a foam pad on which the blood collects and is absorbed.

20. A suction system as recited in claim 19, wherein the foam pad comprises a polyurethane open cell foam pad.

21. A suction system as recited in claim 18, wherein the suction force proportioning means comprises a plurality of ridges protruding from the backing plate towards the attached absorbing means such that channels are formed on the backing plate between the plurality of ridges, the channels extending away from the orifice of the backing plate, and the channels being wider at locations further away from the orifice of the backing plate and more narrow at locations closer to the orifice of the backing plate, thereby distributing the suction force to permit efficient extraction of absorbed fluid from the absorbing means.

22. A suction system as recited in claim 18, wherein the suction force proportioning means comprises a plurality of posts protruding from the backing plate towards the attached absorbing means, wherein channels are formed between the plurality of posts, the channels extending away from the orifice of the backing plate, and the channels being wider at locations further away from the orifice of the backing plate and more narrow at locations closer to the orifice of the backing plate, thereby distributing the suction force to permit efficient extraction of absorbed fluid from the absorbing means.

23. A suction system as recited in claim 18, wherein the backing plate comprises a square shape.

24. A suction system as recited in claim 18, wherein the backing plate comprises a polyvinylchloride plastisol material.

25. A suction system as recited in claim 18, wherein the backing plate comprises a hexagonal shape.

26. A suction system as recited in claim 18, wherein the backing plate comprises an egg shape.

27. A suction system as recited in claim 18, wherein the backing plate comprises an elliptical shape.

28. A suction system as recited in claim 18, wherein the backing plate comprises a round shape which is slightly concave on one side.

29. A suction system as recited in claim 18, wherein the backing plate comprises a triangular shape wherein the corners are rounded.

30. A suction system as recited in claim 18, wherein the backing plate comprises a truncated elliptical shape.

31. A method for absorbing and collecting blood and other interstitial fluids from a surgical site within a patient comprising the steps:
　a. obtaining an apparatus for absorbing and collecting the blood comprising:
　　1) absorbing means for contacting and absorbing the fluid to be collected;
　　2) backing means, attached to said absorbing means, for supporting said absorbing means, said backing means having a substantially centrally positioned orifice formed therein;
　　3) delivery means, attached to the orifice of the backing means, for receiving suction force from a suction source and delivering the suction force to the absorbing means;
　　4) suction force proportioning means, in communication with said backing means and said absorbing means, for distributing the suction force from said suction means such that absorbed fluid is efficiently extracted from the absorbing means;
　b. placing said absorbing means against the area from which the fluid is to be collected;

c. allowing the fluid to be absorbed into the absorbing means;
d. attaching a suction source to said delivery means;
e. operating the suction source such that a suction force is provided through the delivery means to the absorbing means;
f. allowing the suction force proportioning means to disperse the suction force along the absorbing means such that absorbed fluid is efficiently extracted from the absorbing means into the delivery means;
g. collecting the fluid extracted from the absorbing means into a fluid receptacle for later reuse of the collected fluid.

32. A method as recited in claim 31, wherein the suction source is operated intermittently such that the absorbing means is allowed to become substantially soaked with absorbed fluid before the suction is applied.

33. A method as recited in claim 31, wherein the suction source is operated continuously.

* * * * *

UNITED STATES PATENT AND TRADEMARK OFFICE
CERTIFICATE OF CORRECTION

PATENT NO. : 5,437,651
DATED : August 1, 1995
INVENTOR(S) : ROBERT J. TODD et al.

It is certified that error appears in the above-indentified patent and that said Letters Patent is hereby corrected as shown below:

Title page, item [56], column 2, lines 1 and 9, "Throacic" should be --Thoracic--
Column 1, line 27, "continuous" should be --Continuous--
Column 2, line 14, "there beneath" should be --therebeneath--
Column 5, line 5, delete ":"
Column 5, lines 20-23, delete "Again, a length of about 3 inches of a FIG 9 3.0 inches and a width of about 2.0 inches. FIG. 9 illustrates a triangular shape wherein the corners of the triangle are rounded."
Column 5, line 44, after "and" insert --connected to backing plate 16 at orifice 18.--
Column 8, line 2, "a-traumatic" should be --atraumatic--
Column 9, line 57, delete "pl" (PTO error)
Column 9, line 57, "d. delivery means, . . .;" should be a new subparagraph Signed and Sealed this Twenty-sixth Day of March, 1996

Attest:

BRUCE LEHMAN

*Attesting Officer*     Commissioner of Patents and Trademarks